US00PP20016P3

(12) United States Plant Patent
McLaren

(10) Patent No.: US PP20,016 P3
(45) Date of Patent: May 26, 2009

(54) APPLE TREE NAMED 'AB17'

(50) Latin Name: *Malus domestica*
Varietal Denomination: AB17

(75) Inventor: John McLaren, Cromwell (NZ)

(73) Assignee: Nevis Fruit Company Ltd. (NZ)

( * ) Notice: Subject to any disclaimer, the term of this patent is extended or adjusted under 35 U.S.C. 154(b) by 0 days.

(21) Appl. No.: 11/799,787

(22) Filed: May 2, 2007

(65) Prior Publication Data

US 2008/0276338 P1 Nov. 6, 2008

(51) Int. Cl.
*A01H 5/00* (2006.01)

(52) U.S. Cl. ..... Plt./161

(58) Field of Classification Search ..... Plt./161
See application file for complete search history.

*Primary Examiner*—Annette H Para
(74) *Attorney, Agent, or Firm*—Wells St. John P.S.

(57) ABSTRACT

A new and distinct variety of apple tree denominated varietally as 'AB17' which produces fruit which is larger than that produced by the 'Kidd's D-8' apple tree under the ecological conditions prevailing near Ephrata, Wash. and which is further less acidic and which further produces a flower having a purple color with red-purple highlights.

4 Drawing Sheets

Genus and species of the new variety: *Malus domestica.*
Variety denomination: The present variety of apple tree has been denominated 'AB17.'

BACKGROUND OF THE NEW VARIETY

The present invention relates to a new and distinct variety of apple tree which has been denominated varietally as 'AB17'; and more specifically to an apple tree which is principally characterized as to novelty by producing fruit which is larger than that produced by the 'Kidd's D-8' apple tree under the ecological conditions prevailing near Ephrata, Wash., and which is further less acidic, and which further produces a flower having a purple color with red-purple highlights.

ORIGIN AND ASEXUAL REPRODUCTION OF THE NEW VARIETY

The present variety of apple tree 'AB17' resulted from an open pollination of a 'Kidd's D-8' apple tree (U.S. Plant Pat. No. 3,637) in 1986. The seedling was established by me in 1987, on its own root, at my test orchard facility which is located near Central Otago, New Zealand. Following several years of observation of the new selection, budwood was removed and then sent to the NRSP-5 quarantine facility at Prosser, Wash. in March of 1997. In May of 1998, virus-free budwood wood was released and second-generation trees were established by budding onto 'M26' rootstock (unpatented) at a test orchard which is located near Ephrata, Wash. Fruit from these second-generation trees has been observed during the recent five cropping seasons and compared with the fruit earlier produced on the original mother tree, which is still in production at my test orchard in Central Otago, New Zealand. Botanical and pomological comparisons of the fruit produced by the second-generation trees with that of the original mother tree revealed that the second-generation grafted trees produced fruit, and had other botanical characteristics, which appeared to be identical to that displayed by the original mother tree.

SUMMARY OF THE NEW VARIETY

The 'AB17' apple tree is characterized principally as to novelty by producing an attractive bi-colored apple that is somewhat blocky in appearance, but which further has an excellent texture, good sub-acid flavor, and moderate storage life. The present variety matures for harvesting and shipment on or about September $10^{th}$ under the ecological conditions prevailing in the Columbia Basin area of central Washington State. The present variety is easily distinguishable from the fruit produced by 'Kidd's D-8' apple trees (U.S. Plant Pat. No. 3,637). In relative comparison to 'Kidd's D-8' apple trees, the average harvesting date for the most common 'Kidd's D-8' cultivars grown in the same geographical is August $30^{th}$. However, the apples of the new variety are larger than apples produced by the 'Kidd's D-8' apple tree growing at this geographical location. In addition, the apples of the new variety are less acidic than apples produced by the 'Kidd's D-8' apple tree. Furthermore, the new variety produces distinctive flowers having a purple color with red-purple highlights in contrast to the white flowers produced by the 'Kidd's D-8' variety.

BRIEF DESCRIPTION OF THE DRAWINGS

The accompanying drawings are color photographs of various aspects of the present plant. The colors are as nearly true as is reasonably possible in color representations of this type. Due to chemical development, processing, and printing, the leaves and fruit of the present variety may or may not be accurate when compared to the actual specimen. For this reason, future color reference should be made to the color plates as provided by The Royal Horticultural Society, London, and other general color descriptions as provided for, hereinafter.

NOT A COMMERCIAL WARRANTY

Figure 1:
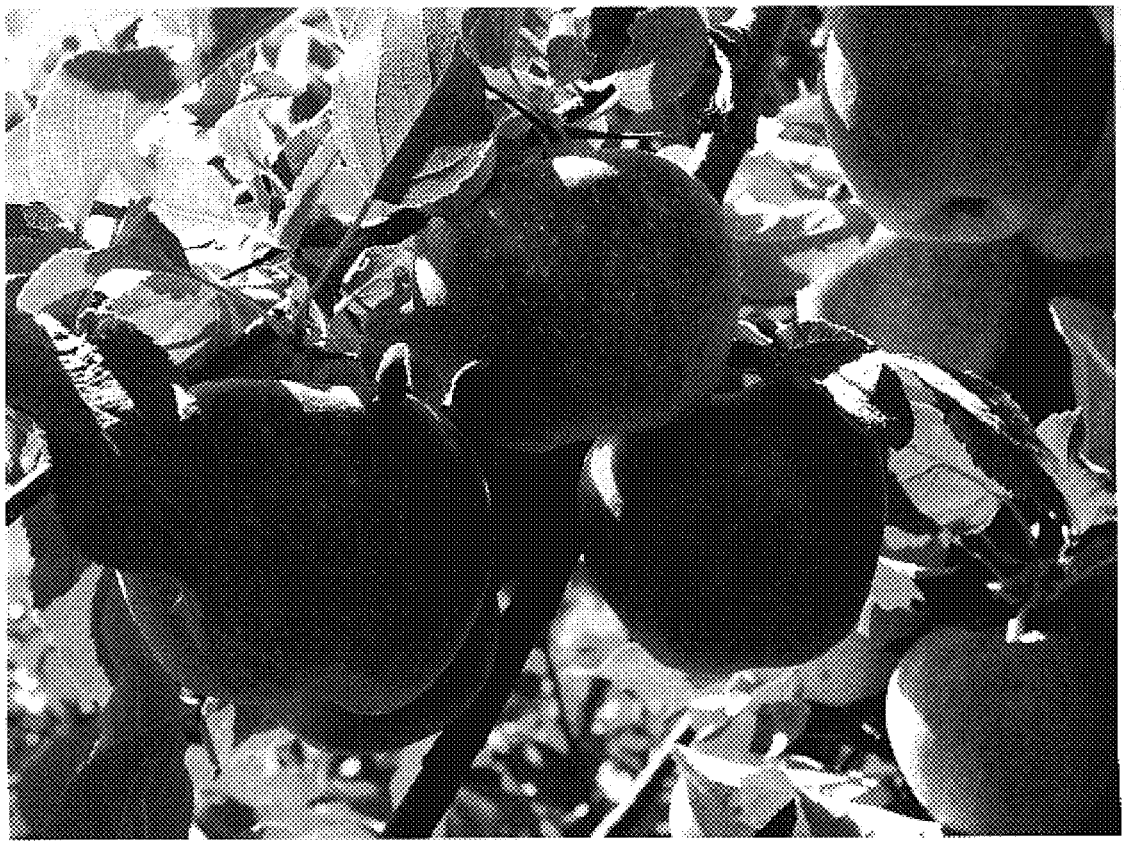
FIG. 1 is a photograph of a fruiting branch of the new variety at near harvest maturity as grown on 'M26' rootstock (unpatented).
Figure 2:
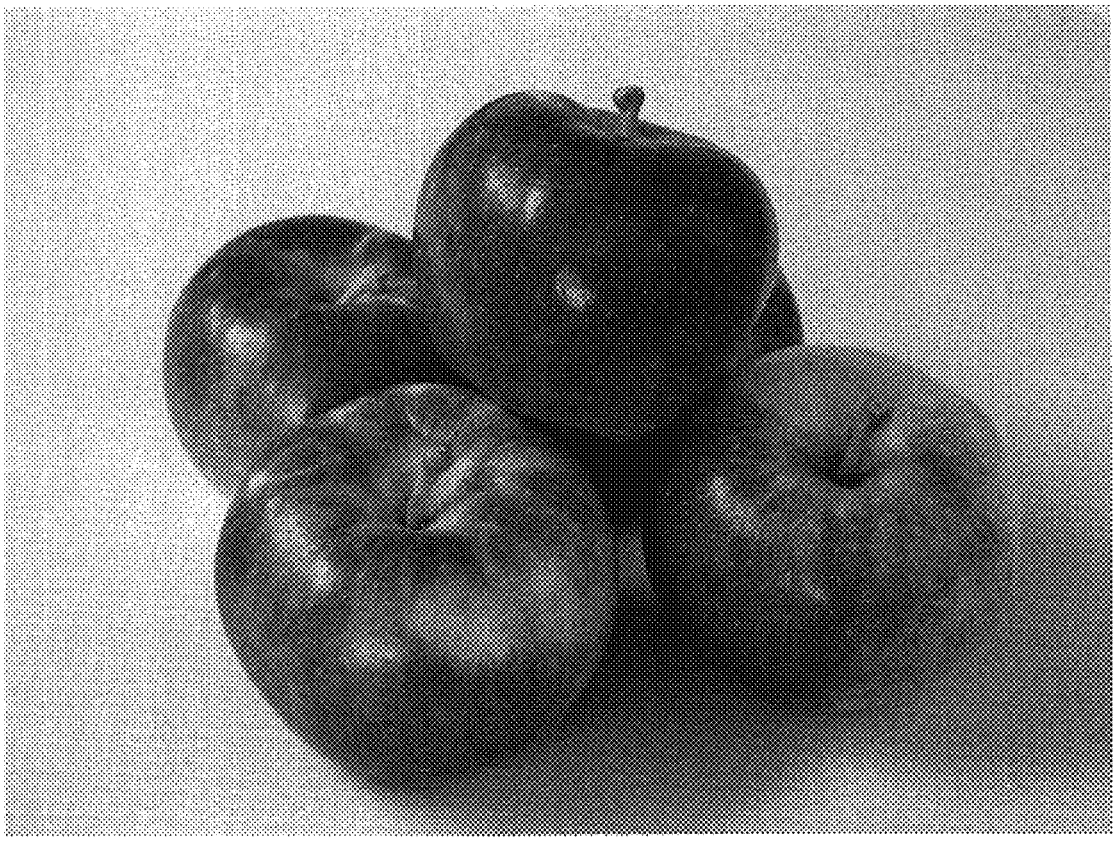
FIG. 2 is a photograph showing the external appearance of harvest mature 'AB17' fruit produced from the second-generation trees now growing on 'M26' rootstock (unpatented).
Figure 3:
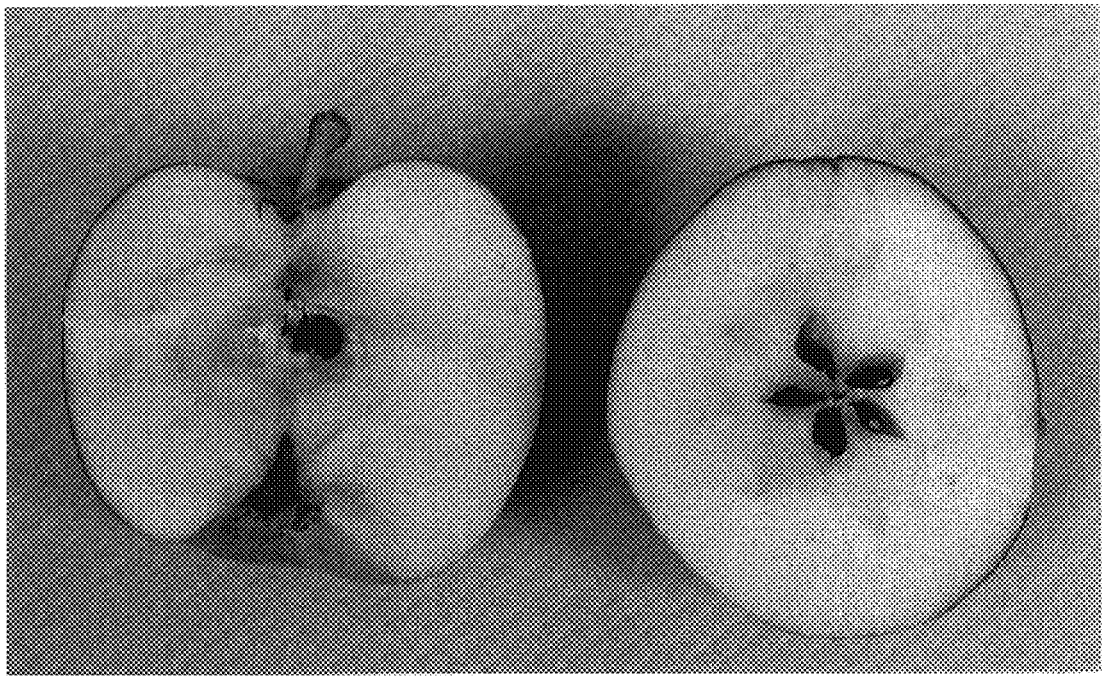
FIG. 3 is a photograph, which exhibits the displayed flesh characteristics of fruit produced by the new variety of apple tree when taken in both the longitudinal and cross sectional planes.
Figure 4:
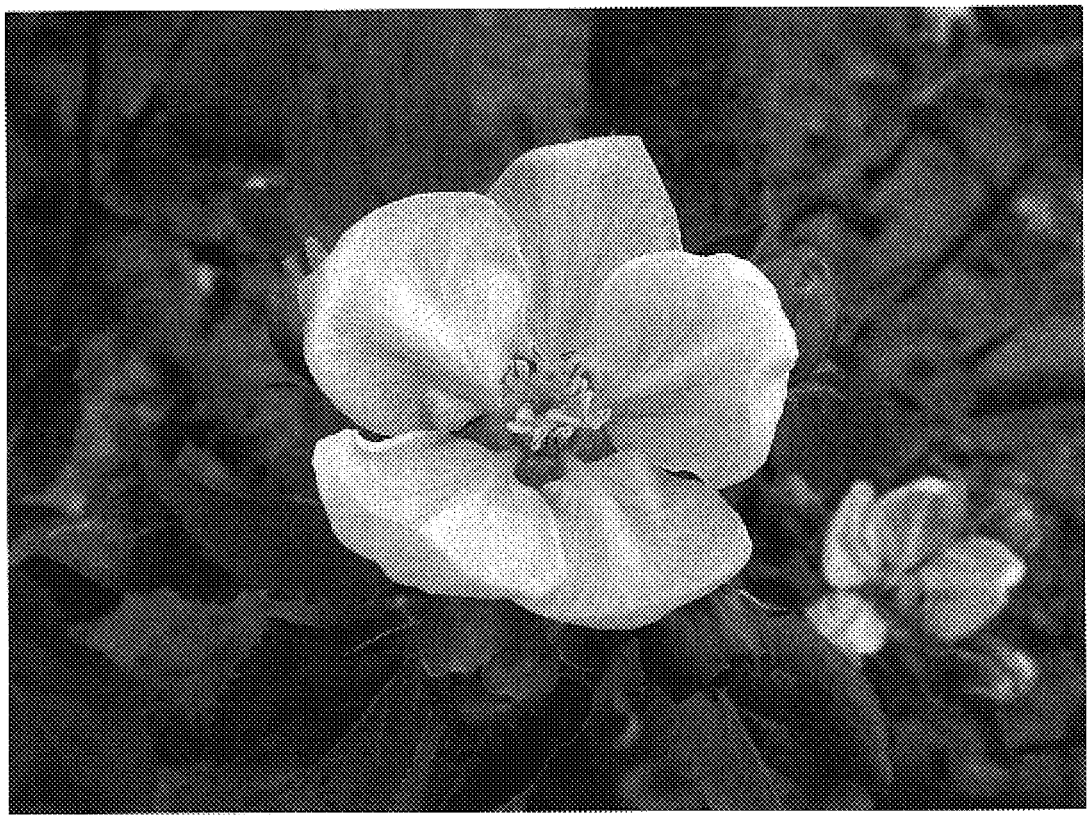
FIG. 4 is a photograph displaying an open flower of 'AB17' of a second-generation 'AB17' apple tree now growing on 'M26' rootstock (unpatented).

The following detailed description has been prepared to solely comply with the provisions of 35 U.S.C. § 112, and does not constitute a commercial warranty (either expressed or implied) that the present variety will, in the future, display the botanical, pomological, or other characteristics as set forth, hereinafter. Therefore, this disclosure may not be relied upon to support any future legal claims including, but not limited to, breach of warranty of merchantability, or fitness for any particular purpose which is directed, in whole, or in part, to the present variety.

DETAILED DESCRIPTION

Referring more specifically to the pomological and botanical details of this new and distinct variety of apple tree, the following was observed during the 2006 growing season under the ecological conditions prevailing in a test orchard, which is located near Ephrata, Wash. At the time of observation the apple tree was eight years old. All major color code designations are by reference to the Royal Horticulture Society Colour Chart (R.H.S.) (3$^{rd}$ Edition) provided by the Royal Horticulture Society of Great Britain.

TREE

*Size.*—Generally — Average as compared to other apple cultivars. The second-generation trees growing at the orchard near Ephrata, Wash. were prepared by grafting the budwood coming from the original mother tree into 'M26' rootstock (unpatented) in 1998. These trees now have a height of about 4.3 meters; and a width of about 2.4 meters. These trees have an overall shape that is spreading and open. The shape of the resulting trees is somewhat dependent upon pruning practices.

*Vigor.*—The present variety is considered moderately vigorous under the current ecological conditions prevailing near Ephrata, Wash.

*Hardiness.*—Generally — Considered hardy under the ecological conditions prevailing in Ephrata, Wash.

*Productivity.*—Generally — Considered medium productive to productive as compared to other cultivars maturing in the same season.

*Regularity of bearing.*—Considered regular.

TRUNK

*Size.*—The average diameter of the trunk when measured at a distance of about 45 cm. above the surface of the earth is about 11 cm. The trunk is considered medium stocky for the variety.

*Bark texture.*—Generally — Considered medium in smoothness.

*Bark color.*—Grey-orange (RHS 164A).

*Bark lenticels.*—Numbers — Considered numerous, and generally horizontal to the plane.

*Bark lenticels.*—Shape — Variable, round and elongated forms may be found. Round bark lenticels have a diameter of about 1.5 mm.

*Elongated bark lenticels.*—Length — About 2 mm. to about 6 mm.

*Elongated bark lenticels.*—Width — About 1 mm.

*Bark lenticels.*—Color — Considered grey-white (RHS 156D).

BRANCHES

*First-year branches.*—Numbers — Considered numerous and generally having no spur development. Scaffold branches are considered moderate in number as compared to other common varieties.

*Crotch angle.*—First-year branches have a crotch angle of about 45 degrees to about 90 degrees. Scaffold branches have a crotch angle of about 65 degrees to about 90 degrees.

*Bark color.*—First-year branches have a yellow green color (RHS 148A). In contrast, scaffold branches have a bark color considered to be grey-orange (RHS 164A).

*Bark lenticels.*—First-year branches — Few in number and elongated in shape. The lenticels have a length of typically about 1 mm. and typically a width of about 0.1 mm. to about 0.3 mm. These bark lenticels are typically vertically oriented.

*Bark lenticel color.*—First-year wood — The color of the bark lenticels is considered white. This color is not considered distinctive of the variety, however.

*Bark lenticel.*—Scaffold branches — The bark lenticels on the scaffold branches are numerous and elongated in shape. These bark lenticels have a length dimension of about 3 mm. to about 5 mm.; and a width dimension of about 1 mm.

*Bark lenticel color.*—Scaffold branches — The color of the bark lenticels is considered white (RHS 155C).

*Bark appearance.*—Areas exhibiting a scaly bark appearance can be found on four to six-year-old wood.

*Branch pubescence.*—First-year wood — Present, considered moderate in amount, and white in color. This color is not distinctive of the variety, however.

*Internodes.*—Spacing — On first-year wood the average spacing is about 3.4 cm.

LEAVES

*Surface texture.*—Considered glabrous and leathery, and having a light rugose on surface.

*Pubescence.*—Generally — May be considered medium in abundance on the ventral surface of the leaf.

*Pubescence color.*—Considered white. This color is not distinctive of the variety, however.

*Average leaf length.*—About 11.6 cm.

*Average leaf width.*—About 7.8 cm.

*Petiole.*—Size — Considered medium long for the variety.

*Petiole.*—Length — About 3.1 cm.

*Petiole.*—Width — As measured at about mid-point along the petiole, about 1.8 mm. Pubescence is present on the petiole.
*Leaf form.*—Considered oval.
*Marginal form.*—Considered doubly serrate.
*Leaf tip.*—Shape — Considered broadly acute.
*Leaf stipules.*—Generally — Normally present, and having a length dimension of about 1 to about 6 mm.; and a width dimension of about 1.3 mm. to about 2.1 mm.
*Leaf color.*—Dorsal surface — Yellow-green (RHS 146A).
*Leaf color.*—Ventral surface — Yellow-green (RHS 146C).

FLOWERS

*Time of bloom.*—Typically about Apr. 29, 2006 under the prevailing ecological conditions existing near Ephrata, Wash.
*Flower size.*—Generally — Considered medium-large for the variety, and having an average diameter of about 47 mm.
*Petal size.*—Width — About 20.7 mm.
*Petal size.*—Length — About 23.2 mm.
*Petal color.*—Considered purple (RHS 76D); and further having highlights from the red-purple group (RHS N66C). This is in stark contrast to the flower produced by the 'Kidd's D-8' apple tree (U.S. Plant Pat. No. 3,637) which is entirely white.
*Stamen.*—Length — In a range of about 4 to 8 mm. with an average length of about 6.8 mm.
*Stamen.*—Color — Considered yellow (RHS 6D).
*Anthers.*—Color — At full maturity, the anthers have a yellow color (RHS 6D).
*Anthers.*—Length — About 2.7 mm.
*Pistil length.*—About 11.5 mm.
*Pistil color.*—Yellow (RHS 6D).
*Styles.*—Numbers — 5, occasionally 6 may be found.
*Styles.*—Form — The styles are typically fused at the base. The base is pubescent.
*Styles.*—Length — About 7.3 mm.
*Styles.*—Color — White from the union down. This color is not distinctive of the variety.
*Stigma.*—Shape — Generally having a rounded top.
*Sepals.*—Form — Curled downwardly and inwardly.
*Sepals.*—Length — About 10.0 mm.
*Sepal pubescence.*—Present and considered white. This color is not distinctive of the variety.
*Sepal.*—Color — Considered green (RHS 143C); and having highlighted tips from the orange-red group (RHS N34A).

FRUIT

*Maturity when described.*—Generally the fruit produced by the present variety is described as it would be found at full commercial maturity. In this regard, the fruit of the present variety was ripe for commercial harvesting and shipment under the ecological conditions prevailing near Ephrata, Wash. on Sep. 10, 2006.
*Fruit size.*—Considered medium large for the species, and having an average diameter of about 8.6 cm.
*Fruit form.*—Considered round conical.
*Fruit stem.*—Generally — Considered short for the species. The stem has an average length of about 1.8 cm.
*Stem cavity.*—Average width — About 4.0 cm.
*Stem cavity.*—Average depth — About 1.9 cm.
*Basin cavity.*—Average width — About 3.8 cm.
*Basin cavity.*—Average depth — About 1.3 cm.
*Calyx.*—Generally — The eye is generally considered divergent.
*Fruit skin.*—Texture — Considered glabrous with a light bloom.
*Fruit skin appearance.*—Bicolor with the overcolor being a mottled blush. The overcolor of the fruit is from the red group (RHS 45D). The undercolor of the fruit is from the green-yellow group (RHS 1D).
*Lenticels.*—Generally — Normally present and moderate in number. The lenticels have a diameter of about 0.3 mm. to about 0.5 mm., and a white color (RSH 155D).
*Core Shape.*—Generally — The core shape is flat across the stem end and decreasing to a point at the apex end thereof.
*Core.*—Position — Considered median and approaching distant.
*Cell shape.*—Considered round and not tufted.
*Tube.*—Shape — Considered cone shaped.
*Sepals.*—Surface texture — Considered downy.
*Stamen Position.*—Generally — Considered median.
*Axis.*—Generally — Axile and closed.
*Seeds.*—Numbers — 1 to 2 seeds per cell are found.
*Seeds.*—Color — Brown (RHS 200B).
*Seeds.*—Shape — Generally considered acute. The seeds have an average diameter of about 4.1 mm.; and an average length dimension of about 6.3 mm.
*Flesh color.*—White. This flesh color is not distinctive of the present variety.
*Flesh firmness.*—Generally — Considered firm yet somewhat melting.
*Flesh flavor.*—Considered mildly sub-acid and delicate. The overall quality of the fruit is considered good.
*Brix.*—At full commercial maturity about 15.4.
*Fruit firmness.*—About 15.8 pounds at full commercial maturity.
*Starch content.*—Based upon a scale of 1–6, and wherein 1 is considered to have a high starch content, and 6 is considered to have no starch, the present variety is considered a 1.8.
*Fruit aroma.*—Considered slightly aromatic and sometimes wanting.
*Keeping quality.*—The present variety has been kept up to 45 days under typical apple storage conditions with no deleterious effects noted.
*Pollination requirements.*—The present variety may be pollinated by any diploid apple tree blooming at about the same blooming season.
*Fruit use.*—Primarily for fresh eating.
*Disease and insect resistance.*—The present variety is considered susceptible to all insects and diseases found in the region of Central Washington.

Although the new variety of apple tree possesses the described characteristics when grown under the ecological conditions prevailing near Ephrata, Wash. in the south central portion of Washington State, it should be understood that variations of the usual magnitude and characteristics incident to changes in growing conditions, fertilizing, pruning, pest control, and horticultural management practices are to be expected.

Having thus described and illustrated my new variety of apple tree, what I claim is new, and desire to secure by plant letters patent is:

1. A new and distinct apple tree variety of apple tree 'AB17' substantially as illustrated and described, and which is characterized principally as to novelty by producing fruit which is larger than that produced by the 'Kidd's D-8' apple tree, U.S. Plant Pat. No. 3637, under the ecological conditions prevailing near Ephrata, Wash. and which is further less acidic and which further produces a flower having a purple color with red-purple highlights.

* * * * *